United States Patent [19]

Stasz

[11] Patent Number: 4,936,281
[45] Date of Patent: Jun. 26, 1990

[54] ULTRASONICALLY ENHANCED RF ABLATION CATHETER

[75] Inventor: Peter Stasz, Moundsview, Minn.

[73] Assignee: Everest Medical Corporation, Brooklyn Center, Minn.

[21] Appl. No.: 337,427

[22] Filed: Apr. 13, 1989

[51] Int. Cl.$^5$ .......................... A61B 8/00; A61B 17/39
[52] U.S. Cl. ............................... 128/660.03; 604/22; 606/48; 606/50
[58] Field of Search ............ 606/41, 45, 46, 48, 606/50; 128/24 A, 660.03, 786; 604/22

[56] References Cited

U.S. PATENT DOCUMENTS

| 3,942,530 | 3/1976 | Northered | 606/46 X |
| 4,674,498 | 6/1987 | Stasz | 606/48 |
| 4,682,596 | 7/1987 | Bales et al. | 606/45 |
| 4,750,902 | 6/1988 | Wuchinich et al. | 604/22 |
| 4,802,476 | 2/1989 | Noerenberg et al. | 604/22 |
| 4,870,953 | 10/1989 | DonMicheal | 128/786 X |

Primary Examiner—Lee S. Cohen
Attorney, Agent, or Firm—Haugen and Nikolai

[57] ABSTRACT

An electrosurgical angioplasty catheter with ultrasonic enhancement is described. It comprises an elongated, flexible plastic tubular body having located at its distal tip an electrode structure for effecting rf cutting along with a transducer for ultrasonically driving the rf cutting electrodes and the support thereof. The electronics module for driving the cutting electrodes and the ultrasonic transducer also includes means for receiving echo signals picked up by the transducer whereby Doppler flow readings and ultrasound imaging of the blood vessel being worked upon can be obtained.

15 Claims, 2 Drawing Sheets

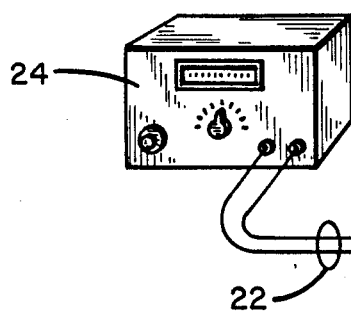
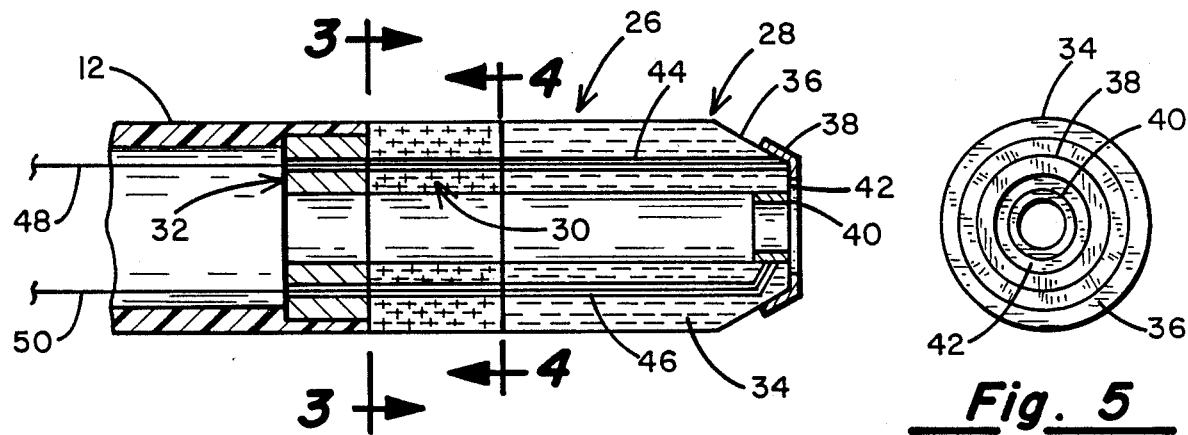
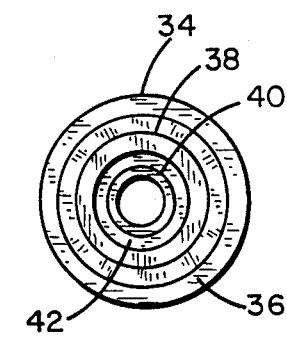
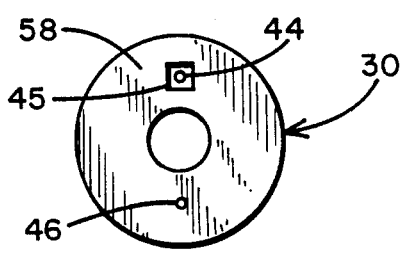
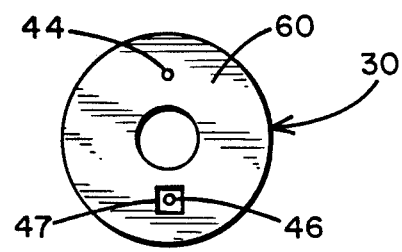
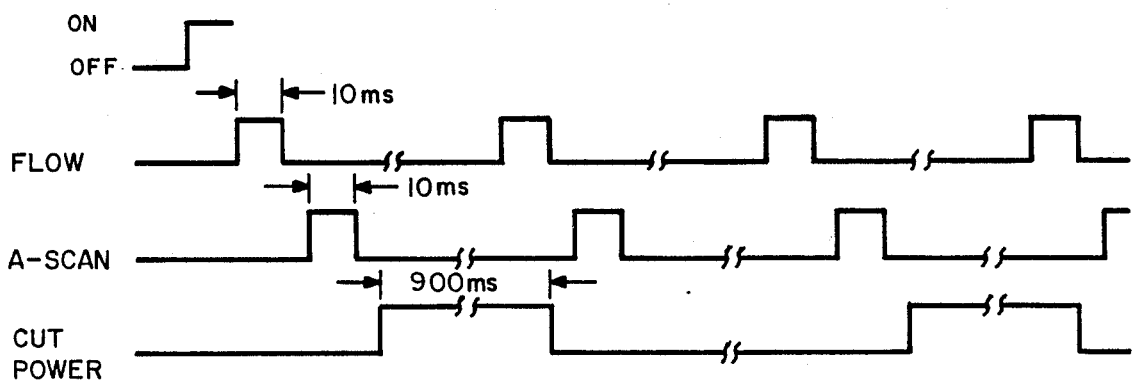

ULTRASONICALLY ENHANCED RF ABLATION CATHETER

BACKGROUND OF THE INVENTION

Field of the Invention

This invention relates generally to electrosurgical apparatus and more particularly to an improved intravascular catheter which can be used to effectively remove both fatty deposits and more calcified lesions from the interior walls of a blood vessel.

Discussion of the Prior Art

The buildup of atheromas or the formation of thrombi in a blood vessel can cause serious circulatory problems and when complete blockage occurs, distal tissues may be deprived of oxygen and nutrients, leading to damage or destruction of cell tissue downstream of the blockage. As the blockage grows, distal tissue may become more ischemic unless, of course, channelization occurs whereby blood bypasses the constriction. With a narrowed blood vessel, a point may be reached where even a tiny thrombus becomes lodged creating an infarct.

The treatment of diseased blood vessels depends to a large extent on the location of the blockage. In the case of a blocked or partially blocked coronary artery, it has been the practice to perform coronary bypass surgery. In a like fashion, blood vessel shunts have been installed in other body areas as well. The surgery involved in those procedures tends to be quite traumatic, involving, in the case of coronary-bypass surgery, the opening of the patient's chest and pericardium. In treating deep vein thrombosis or other blockages in the peripheral vasculature, extensive excision and vessel replacement is often required.

More recently, following the technique credited to A. Grunzig, a balloon catheter has been used to restore patency to blood vessels without extensive surgery. In carrying out this technique, a catheter having a small inflatable balloon on its distal end is routed through the vascular system to the site of the restriction to be treated. The deflated balloon is appropriately positioned to span the blockage in question and then a fluid is introduced into the proximal end of the catheter to inflate the balloon to a sufficiently high pressure whereby the blockage is spread open and patency is restored.

As is pointed out in the U.S. Pat. No. 4,445,509 to Auth, there are some deficiencies in the Grunzig procedure which renders it ineffective in certain applications. For example, the blockage may be such that it is not possible to safely force the distal tip of the catheter through the blockage prior to the inflation of the balloon. The Auth patent also cites a number of other U.S. patents relating to catheter-mounted cutting devices intended to "tunnel" through a blockage but without doing damage to the healthy blood vessel tissue. The invention of the Auth patent is in the design of a rotatably driven cutting tool which will preferentially abrade hard or calcified lesions while not significantly abrading the endothelial lining of the blood vessel.

Atherectomy catheters with rotary cutting heads are difficult and costly to make, especially given the need for providing seals on shafts moving at very high speeds. The RF ablation catheter of the present invention is substantially easier to produce in that no moving parts are involved. Also, the debris released downstream from rotating cutters may be substantial, whereas debris from RF ablation is very small and more easily tolerated by the body.

OBJECTS

It is accordingly a principal object of the present invention to provide an improved angioplasty catheter for use in removing unwanted tissue deposits from the interior walls of blood vessels.

Another object of the invention is to provide an angioplasty catheter in which rf energy is applied across a pair of spaced bipolar electrodes to effect electrosurgical cutting.

Yet another object of the invention is to provide an electrosurgical catheter including an ultrasonic transducer for imparting high frequency vibrations to the tissue as electrosurgical cutting takes place.

A further object of the invention is to provide an electrosurgical catheter having a distal tip member with bipolar electrodes as well as ultrasonic transducing means whereby Doppler flow measurements and/or a A-scan image of the site to be treated can be realized.

Still another object of the invention is to provide an improved angioplasty catheter which can be readily manufactured using state-of-the-art techniques and which portends greater safety and efficacy than certain prior art surgical implements intended for the same end-use.

SUMMARY OF THE INVENTION

The foregoing features, objects and advantages are realized by providing an elongated, flexible, plastic tubular body member having a proximal end and a distal end and with at least one lumen extending from the proximal end to its distal end. A tip member is secured to the distal end of the tubular body member and includes a ceramic tube having a beveled distal end portion supporting a pair of spaced electrodes. These electrodes comprise a bipolar pair and are adapted to be driven by an electrosurgical generator located at the proximal end of the catheter. Abutting the ceramic tube on which the bipolar electrodes are affixed is a piezoelectric transducer, which may be energized by the same signal generator, for producing ultrasonic vibrations of the tip. The transducer is split so that one portion thereof may be made to selectively function as a transmitting transducer while the second half functions as a receiving transducer. The receive signals are fed back to the electronics module at the proximal end of the catheter whereby both Doppler shifts proportional to blood flow rates and A-scan information can be processed for display.

The tip member further includes a back-up plate abutting the piezoelectric transducer which functions to enhance the ultrasonic power output characteristics of the catheter.

DESCRIPTION OF THE DRAWINGS

A better understanding of the construction and operational characteristics of the invention can be realized from a reading of the following detailed description especially in light of the accompanying drawings in which like numerals in the several views refer to corresponding parts.

FIG. 1 is a general mechanical diagram of the ultrasonically enhanced electrosurgical angioplasty catheter system of the present invention;

FIG. 2 is a greatly enlarged cross-sectional view taken along the lines 2—2 in FIG. 1;

FIG. 3 is a cross-sectional view taken along the lines 3—3 in FIG. 2;

FIG. 4 is a cross-sectional view taken along the lines 4—4 in FIG. 2;

FIG. 5 is an end view of the catheter tip illustrated in FIG. 2;

FIG. 7 constitutes a timing diagram helpful in explaining the operation of the circuit of FIG. 6.

DESCRIPTION OF THE PREFERRED EMBODIMENT

Figure 6:
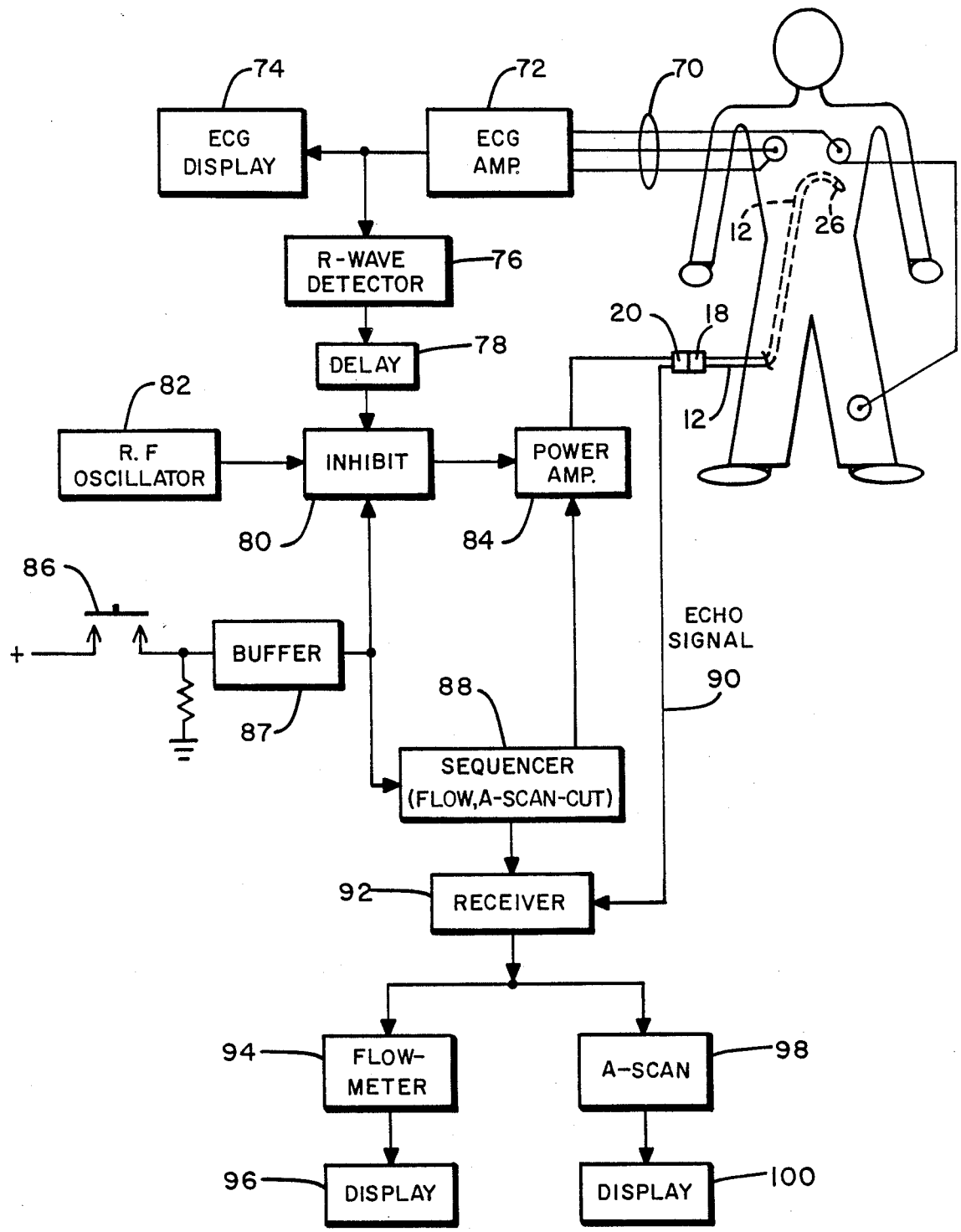
FIG. 6 is a general block diagram of the electrosurgical generator which may be used to drive the electrosurgical catheter.

Referring first to FIG. 1, there is illustrated generally by numeral 10 an electrosurgical catheter in accordance with the present invention. It includes an elongated flexible plastic tubular member 12 having a proximal end 14 and a distal end 16. The proximal end is provided with a suitable electrical/mechanical connector 18 adapted to mate with a corresponding connector 20 which is connected by cables 22 to the outputs of an electrosurgical generator 24.

The catheter body 12 may be made from a variety of materials including silicon rubber, polyurethane, Teflon ®or any other appropriate plastics commonly used in constructing intravascular catheters. Its outside dimensions will be such as to permit it to be routed through the vascular system from an entrance site, e.g., the femoral artery, to a treatment site, e.g., a coronary blood vessel.

Affixed to the distal end 16 of the tubular body 12 is a distal tip member 26, the constructional features of which are best illustrated in the greatly enlarged, cross-sectional view of FIG. 2. The tip member 26 comprises three major sections, namely: an RF cutter means 28, a piezoelectric transducer means 30 and a transducer backup means 32.

Considering first the distally disposed RF cutter means 28, it comprises a tubular body 34 which is preferably fabricated from a ceramic such as silicon nitride because of that material's enhanced thermoconductivity characteristics as compared to other ceramics. The distal end portion of the tubular ceramic body 34 is beveled at a predetermined angle, e.g. 45°, and affixed to the beveled nose portion 36 thereof is a first electrically conductive annular electrode 38. The electrode 38 may be formed from a number of metals, such as platinum, silver, tungsten, titanium, nickel, stainless steel and may be formed using a variety of known processes including, but not limited to, silk screening, vapor deposition, plasma spraying. Disposed within the lumen of the ceramic tube 34 is a second annular electrically conductive electrode means 40. Electrode 40 is separate from the electrode 38 by a predetermined gap 42 of exposed ceramic.

Each of the backup plate 32, the piezoelectric transducer means 30 and the RF cutter means 28 is provided with a pair of longitudinal bores 44 and 46 which are aligned with one another permitting electrical conductors 48 and 50 coming from the proximal connector 18 to reach and connect to the distal tip bipolar electrodes 38 and 40. In this manner, rf energy from the signal generator 24 can be impressed across the bipolar electrodes 38 and 40 to create a high intensity current path therebetween for performing RF ablation of the tissue coming in contact with the distal end of the tip member 28.

By beveling the ceramic tubular substrate, the gap between the electrodes 38 and 40 can be made quite small with physical strength perhaps becoming a limiting factor. Also, the somewhat pointed end of the tip member 34 facilitates its being threaded through the blood vessel. By tapering the ceramic in the fashion indicated, current flow through the ceramic itself is minimized in that the capacitance is lowered. As such, the current is better directed into the tissue load rather than through the ceramic. Moreover, the sonic energy emitted from the distal edge of the tip member 28 tends to be more focused or concentrated than if no bevel is provided on the ceramic tube.

FIGS. 3 and 4 respectively show the proximal and distal side surfaces of the piezoelectric transducer 30. The transducer is preferably formed of a crystalline lead-titinate-zirconate ceramic. The transducer has its side surfaces covered with a metal electrode. The electrode 58 on the proximal face (FIG. 3) may comprise a deposited metal such as silver. Likewise, the distal edge surface shown in FIG. 4 is also provided with a conductive electrode material as at 60.

The conductor 50 may be considered RF common and in passing through the bore 46 is electrically joined to the electrode surface 58. It also passes through the electrode surface 60, but no electrical connection is made between it and RF common conductor 50. Instead, conductor 50 extends through the extension of bore 46 in the ceramic tubular member 34 to connect to the ring electrode 40. Wire 48 extends through the bore 44 and is insulated from the electrode surface 58 while being electrically joined to the electrode surface 60. Wire 48 also extends beyond the piezoelectric transducer 30, through the extension of bore 44 in the tubular ceramic substrate 34 and is electrically joined to the annular bipolar electrode 38.

With the conductors 48 and 50 connected as described, when it is desired to perform a Doppler flow measurement or to obtain a Type A scan within the vascular branch in which the tip member 26 is positioned, the generator 24 causes a pulse of RF energy to be applied across the transducer 30, via the RF common conductor 50 and the conductor 48. The voltage pulse causes an acoustic signal to be generated which is reflected in part from the obstruction, the reflected energy impinging back upon the transducer 30. The resulting electrical signal developed between the electrode 60 and the RF common electrode 58 is then fed back over conductors 48 and 50 to the electronics module 24 for processing, readout and display.

If it is desired to effect RF cutting, an RF signal is applied between the RF common conductor 50 and the conductor 48 whereby the requisite RF voltage is developed across the tip electrodes 38 and 40 to create an arc discharge or, at least, a current concentration sufficient to effect cutting. This same RF signal is also impressed across the transducer 30, causing it to impart ultrasonic vibrations to the ceramic tube 34 carrying the cutting electrodes 38 and 40. The combination of the RF cutting with the ultrasonic vibrations has been found to produce improved plaque removal than when only RF electrosurgical cutting is employed. The ultrasonic vibrations tend to prevent the buildup of charred tissue across the electrodes, providing a more uniform current distribution between the bipolar pair.

Improved ultrasonic wave generation is achieved when the three sections 28, 30 and 32 bear a predetermined length relationship with one another and with the wavelength, λ, of the applied RF drive signal. Specifically, it has been found that if the working tip 28 is of a length (¼) λ or (¾) λ, standing waves are effectively maximized and acoustic power output is maximized.

While the use of closely-spaced, bipolar electrodes 38 and 40 tends to limit the length of the return path through the body and because of the frequency employed, it is quite unlikely that the use of the system of the present invention in performing cardiac angioplasty would result in equipment driven tachycardia or ventricular fibrillation. However, to further limit that possibility, it may prove convenient to synchronize the application of the RF energy with the patient's own cardiac cycle. In this way, steps can be taken to inhibit operation during the so-called vulnerable period of the heart. To achieve this result, a three-lead ECG electrode output is fed over conductors 70 to the input of an ECG amplifier 72 (FIG. 6). If desired, the patient's ECG waveform can be displayed on an appropriate terminal 74. A R-wave detector 76 receives the output from the ECG amplifier 72 and, after a predetermined delay 78, produces a signal to the inhibit circuit 80. The inhibit circuit 80 is connected to the low-power side of the RF oscillator 82 and functions to block the output from the oscillator 82 from reaching the power amplifier 84. By appropriately establishing the delay 78 relative to the occurrence of the R-wave as picked up by the detector 76, the inhibit circuit 80 can be made to become operative to perform its specified function following the normal refractory period of the heart and just before the onset of the T-wave.

The output from the power amplifier 84 feeds through the connector 20/18 and through the conductors 48 and 50 (FIG. 2) to effect either a blood flow reading, an A-scan image of the treatment site or to effect RF cutting coupled with the enhancing ultrasonic vibration. More particularly, when the switch 86 is closed, a sequencer circuit 88 is initiate via buffer circuit 87.

Looking at the waveforms of FIG. 7, the sequencer may be designed to first apply a burst of RF energy across the conductors 48 and 50 to cause the transducer 30 to vibrate and produce an acoustic wave to project from the distal tip of the ceramic tubular substrate member 34. This acoustic wave will propagate through the blood flowing through the vessel and a portion of that energy will be reflected back from moving red blood cells and the like to impinge upon the transducer 30. An electrical signal is thereby developed between the RF common electrode 48 and 50 over the line 90 (FIG. 6) to the input of a receiver 92. The receiver 92 includes conventional amplifying and filtering circuitry commonly used with Doppler flow metering equipment 94 and together they analyze the Doppler shift between the transmitted frequency and the received frequency to thereby derive an output proportional to flow rate. This output may conveniently be displayed on a conventional display terminal 96.

At a subsequent point in time, the sequencer 88 enables the power amplifier 84 to again drive the piezoelectric transducer 30 with the echo signal this time being used to develop an A-scan presentation and display via the modules 98 and 100. The amplitude of the A-scan echo reflects the tissue characteristics while the width of the echo pulse is indicative of the thickness of the blocking tissue. The distance along the time axis between the transmitted pulse and the received echo is indicative of distance of the blockage from the distal end of the catheter.

Typically, when performing ultrasonic Doppler flow meter measurements and an A-scan imaging, improved resolution results when the transducer is driven at a relatively high frequency, e.g., 2 to 4 MHz. However, a somewhat lower frequency, for example, about 100 KHz results in improved cutting. Therefore, it is contemplated that the RF oscillator 82 and power amplifier 84 be capable of operating in the above two frequency ranges. It is also contemplated that the ultrasonic transducer 30 be split along a diameter thereof to effectively divide the crystal into two halves. The halves would then be bonded together with a suitable insulating material, such as epoxy. The RF common electrode 58 would be made to bridge both halves while the electrode surface 60 would also be split into two separated, insulated halves. In this fashion, one segment of the transducer can be used as a signal transmitting element while the other half simultaneously functions as a receiving element. When using this latter approach, the electronic circuitry for the ultrasonic imaging and flow measurements is greatly simplified and the need to toggle the electronics between a transmitting mode and a receiving mode is obviated. On the other hand, when using the ultrasonic vibrations of the electrosurgical tip, both halves of the transducer are simultaneously powered.

Experiments have shown that RF cutting alone without ultrasonic vibration works fairly well in soft, fatty tissue. On the other hand, ultrasonic energy with no simultaneous RF arcing across the bipolar electrodes is most effective in hard, calcified tissue. When an RF arc and ultrasound are simultaneously applied, it is effective in ablating lesions which comprise a combination of both hard and soft tissues.

By extending the lumen of the tubular catheter body 12 through the back-up member 32, the transducer 30 and the ceramic base 28 and the center of electrode 40, it is also possible to perfuse blood during the treatment to distal tissues or to inject a contrast medium. It can also be used to aspirate the treatment site to capture and remove tissue debris which may result.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical angioplasty catheter, comprising:
   (a) an elongated, flexible, plastic tubular body member having a proximal end, a distal end and at least one lumen extending from said proximal end to said distal end; and
   (b) a tip member secured to the distal end of said tubular body member, said tip member including
      (i) means for effecting rf cutting; and
      (ii) means for ultrasonically driving said rf cutting means with vibratory forces.

2. The electrosurgical angioplasty catheter as in claim 1 wherein said means for effecting rf cutting comprises:
  (a) a cylindrical ceramic tube having a lumen extending longitudinally therethrough, a proximal end and a beveled distal edge supporting a first annular conductive electrode thereon with a second annular electrode disposed in said lumen of said ceramic tube whereby a predetermined insulating spacing is maintained between said first and second electrodes;
  (b) conductor means extending from said proximal end of said tubular body, through said tubular body and said tip member and connected to said first and second electrodes; and
  (c) means for applying a predetermined rf voltage to said conductor means.

3. The electrosurgical angioplasty catheter as in claim 2 wherein said ceramic tube is fabricated from materials selected from the group consisting of silicon nitride and aluminum nitride.

4. The electrosurgical angioplasty catheter as in claim 2 wherein said means for ultrasonically driving said rf cutting means comprises:
  (a) a cylindrical piezoelectric ceramic transducer having a proximal end and a distal end, each including an electrode surface in contact with said conductor means, said distal end of said transducer abutting said proximal end of said ceramic tube; and
  (b) a back-up plate abutting said proximal end of said transducer for directing said vibratory forces produced by said transducer toward said ceramic tube.

5. The electrosurgical angioplasty catheter as in claim 4 wherein the length dimensions of said back-up plate, said ceramic transducer and said ceramic tube bear a predetermined relationship to the frequency of said rf voltage.

6. The electrosurgical angioplasty catheter as in claim 5 wherein said predetermined relationship is such that the length dimensions of said back-up plate, said transducer and said ceramic tube are $\lambda 4$, $\lambda 2$ and either $\lambda 4$ or $3\lambda/4$, respectively, where $\lambda$ is the wavelength of said rf voltage.

7. The electrosurgical angioplasty catheter as in claim 4 wherein said cylindrical ceramic piezoelectric transducer comprises first and second segments of generally semicircular cross-section, said segments being joined together with an electrically insulating medium along a longitudinal, medial plane.

8. The electrosurgical angioplasty catheter as in claim 4 wherein said cylindrical ceramic piezoelectric transducer and said back-up plate each include a central longitudinal bore aligned with said lumen of said ceramic tube and with said lumen of said tubular body member.

9. The electrosurgical angioplasty catheter as in claim 8 and further including a pair of further separate longitudinal bores extending through said back-up plate, said transducer and said ceramic tube parallel to said central longitudinal bore with said conductor means extending through said further separate bores.

10. The electrosurgical angioplasty catheter as in claim 2 wherein said first and second annular electrodes are made from materials selected from the group consisting of stainless steel, platinum, palladium, titanium, nickel, gold, silver, molybdnum and alloys thereof.

11. An electrosurgical rf angioplasty catheter for removal of atherostenotic lesions comprising:
  (a) an elongated flexible, plastic catheter body having an outer diameter sufficiently small to pass through portions of the vascular system of a living being, a proximal end, a distal end and a central lumen extending between said proximal end and said distal end;
  (b) a tip member bonded to said distal end of said catheter body, said tip member including a proximally disposed back-up plate, a distally disposed ceramic member supporting first and second spaced part electrodes comprising a bipolar electrode pair, and piezoelectric crystal transducer means disposed between said back-up plate and said ceramic member for imparting vibrational forces to said ceramic member;
  (c) electronic means disposed at said proximal end of said catheter body and coupled to said transducer means for generating pulses of ultrasonic energy in a medium in which said tip member is immersed and for receiving electrical signals produced by said transducer means upon receipt of reflected energy whereby low rates of said medium can be measured and features of said vascular system displayed; and
  (d) means including said electronic means for simultaneously energizing said transducer means and said bipolar electrode pair with rf power whereby electrosurgical cutting of said atherostenotic lesions occurs as ultrasonic energy impinges on said lesions.

12. The rf electrosurgical angioplasty catheter as in claim 11 and further including means for synchronizing said electronic means to the ECg cycle of said living being.

13. A method of removing unwanted tissue deposits from the interior walls of a selected blood vessel of a patient's vascular system comprising the steps of:
  (a) inserting an rf electrosurgical catheter into said patient's vascular system, said catheter comprising an elongated flexible tubular member having a proximal end, a distal end and a tip member attached to said distal end of said tubular member, said tip member including a non-conductive base supporting a pair of bipolar electrodes and ultrasonic transducer means positioned to impart vibrational forces to said base;
  (b) advancing said catheter until said tip member is positioned adjacent said tissue deposit; and
  (c) applying rf energy across said bipolar electrodes to produce a high current flow between said electrodes while simultaneously driving said ultrasonic transducer means with rf energy.

14. The method as in claim 13 and further including the steps of:
  (a) energizing only said ultrasonic transducer means with rf energy to generate an acoustic wave in said blood vessel;
  (b) detecting reflected acoustic waves within said blood vessel with said transducer means for determining the size position and consistency of said tissue deposit.

15. The method as in claim 13 and further including the steps of:
  (a) energizing only said ultrasonic transducer means with rf energy to generate an acoustic wave in said blood vessel; and
  (b) detecting reflected acoustic waves within said blood vessel with said transducer means determining the rate of flow of blood through said blood vessel.

* * * * *

UNITED STATES PATENT AND TRADEMARK OFFICE
CERTIFICATE OF CORRECTION

PATENT NO. : 4,936,281
DATED : June 26, 1990
INVENTOR(S) : Peter Stasz

It is certified that error appears in the above-identified patent and that said Letters Patent is hereby corrected as shown below:

Column 8, line 20, change "low" to -- flow --.

Signed and Sealed this

Eighteenth Day of June, 1991

*Attest:*

*Attesting Officer*

HARRY F. MANBECK, JR.

*Commissioner of Patents and Trademarks*